US 6,623,496 B2
\*Sep. 23, 2003

(12) United States Patent
Snow et al.

(10) Patent No.: US 6,623,496 B2
(45) Date of Patent: \*Sep. 23, 2003

(54) ATHERECTOMY CATHETER WITH ALIGNED IMAGER

(75) Inventors: David W. Snow, San Carlos, CA (US); James R. Flom, San Francisco, CA (US)

(73) Assignee: Fox Hollow Technologies, Inc., Redwood City, CA (US)

( \* ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/930,372

(22) Filed: Aug. 14, 2001

(65) Prior Publication Data

US 2002/0077647 A1 Jun. 20, 2002

Related U.S. Application Data

(63) Continuation of application No. 09/378,224, filed on Aug. 19, 1999, now Pat. No. 6,299,622.

(51) Int. Cl.[7] ................................................. A61D 1/02
(52) U.S. Cl. ..................................................... 606/159
(58) Field of Search ................................. 606/159, 169, 606/170, 180, 171, 174, 184; 604/22

(56) References Cited

U.S. PATENT DOCUMENTS

| 33,258 A | 7/1861 | Onik et al. |
|---|---|---|
| 505,210 A | 4/1893 | Clement |
| 2,178,790 A | 11/1939 | Henry |
| 3,705,577 A | 12/1972 | Sierra |

(List continued on next page.)

*Primary Examiner*—Kevin T. Truong
(74) *Attorney, Agent, or Firm*—Townsend and Townsend and Crew, LLP

(57) ABSTRACT

An atherectomy catheter is provided for excising and imaging material in a body lumen. In one embodiment, the catheter comprises a catheter body, a cutting blade, and an imaging device. The cutting blade is mounted on the catheter body and configured to move between a first position and a second position relative to an aperture or cutting window. When the cutting blade is in the second position, the blade substantially closes the aperture on the catheter body. The imaging device which is mounted on or otherwise coupled to the cutting blade is configured to be in an imaging position when the cutting blade substantially closes the aperture or cutter window. This allows the imaging device to survey material within the cutting zone of the atherectomy catheter. By allowing the imaging device to view materials within this cutting zone, material may be imaged and then removed from the body lumen without having to reposition the catheter between each step.

18 Claims, 9 Drawing Sheets

U.S. PATENT DOCUMENTS

| | | |
|---|---|---|
| 3,815,604 A | 6/1974 | O'Malley et al. |
| 3,837,345 A | 9/1974 | Matar |
| 3,995,619 A | 12/1976 | Glatzer |
| 4,210,146 A | 7/1980 | Banko |
| 4,696,298 A | 9/1987 | Higgins et al. |
| 4,781,186 A | 11/1988 | Simpson et al. |
| 4,819,635 A | 4/1989 | Shapiro |
| 4,850,957 A | 7/1989 | Summers |
| 4,979,951 A | 12/1990 | Simpson |
| 4,994,067 A | 2/1991 | Summers |
| 5,024,651 A | 6/1991 | Shiber |
| 5,087,265 A | 2/1992 | Summers |
| 5,224,488 A | 7/1993 | Neuffer |
| 5,226,910 A | 7/1993 | Kajiyama et al. |
| 5,242,460 A * | 9/1993 | Klein et al. .................... 604/22 |
| 5,250,059 A | 10/1993 | Andreas et al. |
| 5,250,065 A | 10/1993 | Clement et al. |
| 5,285,795 A | 2/1994 | Ryan et al. |
| 5,312,425 A | 5/1994 | Evans et al. |
| 5,318,528 A | 6/1994 | Heaven et al. |
| 5,395,313 A | 3/1995 | Naves et al. |
| 5,431,673 A | 7/1995 | Summers et al. |
| 5,507,292 A * | 4/1996 | Jang et al. .................... 606/159 |
| 5,571,122 A | 11/1996 | Kelly et al. |
| 5,571,130 A | 11/1996 | Simpson et al. |
| 5,584,842 A | 12/1996 | Fogarty et al. |
| 5,620,447 A | 4/1997 | Smith et al. |
| 5,634,464 A | 6/1997 | Jung et al. |
| 5,665,098 A | 9/1997 | Kelly et al. |
| 5,674,232 A | 10/1997 | Halliburton |
| 5,695,506 A | 12/1997 | Pike |
| 5,709,698 A | 1/1998 | Adams et al. |
| 5,733,296 A | 3/1998 | Rogers et al. |
| 5,843,103 A | 12/1998 | Wulfman |
| 6,022,362 A * | 2/2000 | Lee et al. .................... 606/159 |
| 6,036,656 A | 3/2000 | Slater |
| 6,036,707 A | 3/2000 | Spaulding |

* cited by examiner

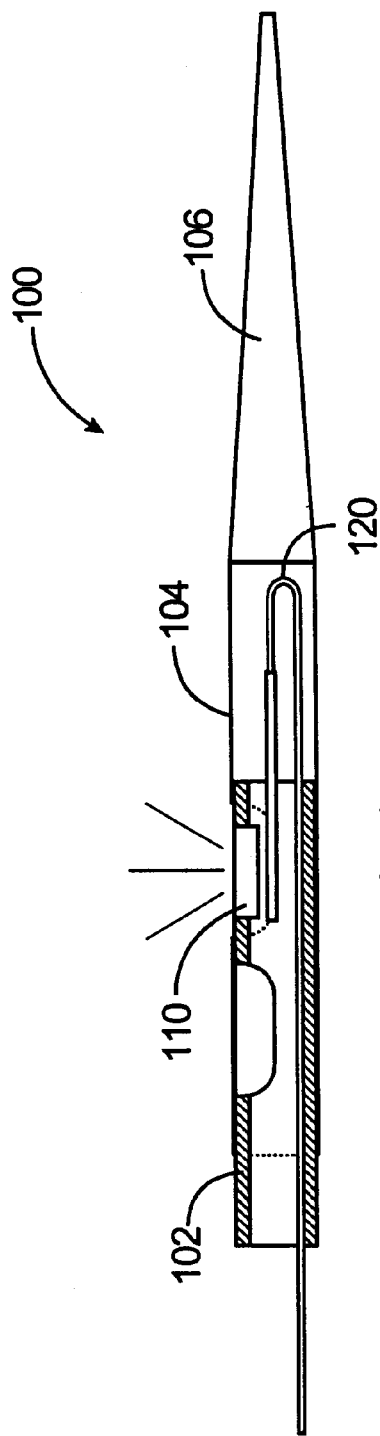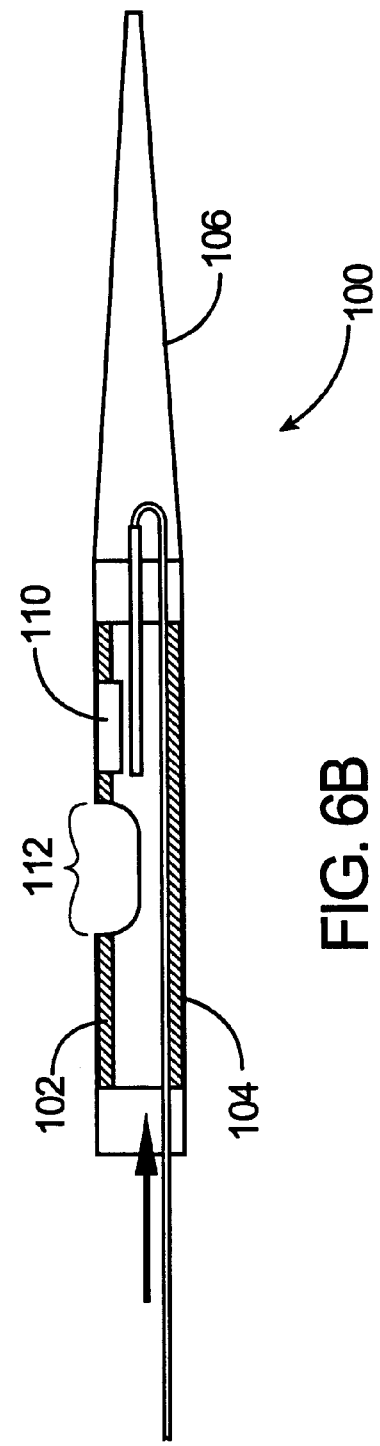

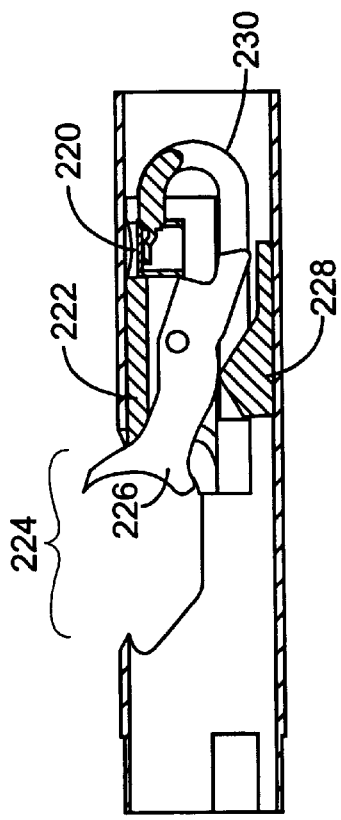
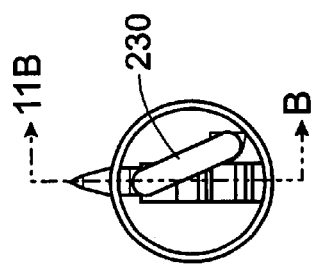
FIG. 11B
FIG. 11A
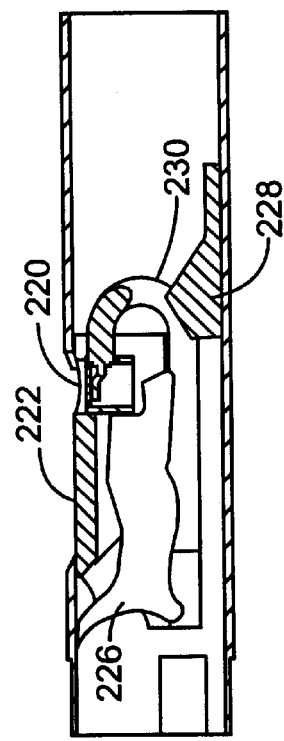
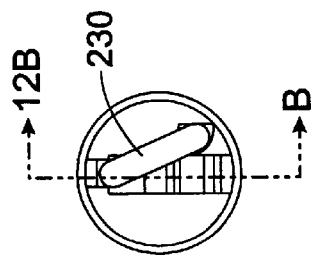
FIG. 12B
FIG. 12A

ATHERECTOMY CATHETER WITH ALIGNED IMAGER

CROSS-REFERENCES TO RELATED APPLICATIONS

This application is a continuation of U.S. Ser. No. 09/378,224, filed Aug. 19, 1999, the full disclosures of which are incorporated herein by reference.

BACKGROUND OF THE INVENTION

The present invention relates generally to apparatus and methods for removing occluding materials from body lumens. More particularly, the present invention relates to the construction and use of atherectomy catheters with an ability to view atheroma and other materials to be excised from blood vessels.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

Atherosclerosis can be treated in a variety of ways, including drugs, bypass surgery, and a variety of catheter-based approaches which rely on intravascular widening or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon or other deflecting structure to urge the aperture against the material to be removed.

Although atherectomy catheters have proven to be very successful in treating many types of atherosclerosis, existing catheter designs may be further improved to provide enhanced performance. For example, in nibbler-type atherectomy catheters and in material excising devices in general, it would be desirable to view the material to be removed prior to the removal step. Furthermore, it would be advantageous if this imaging capability were provided on the same catheter or device which performed the cutting procedure, thus reducing the amount of surgery time spent exchanging imaging and cutting devices. Although some existing catheters provide imaging capability, these devices generally require repositioning of the catheter and the cutting element between imaging and cutting procedures. This undesirably limits the ability of the surgeon to view the exact area of occlusive material to be removed prior to the cut. Such known devices also typically cause the user to first scan a large, less precise area of body lumen. It would be desirable if the device could image the precise area to be excised immediately preceding the cut. Additionally, the repositioning of the entire catheter between imaging and cutting may cause the cutting element to remove material from a location different than the one that was imaged. This decreases the effectiveness of the cutters and may accidentally damage the body lumen. Known imaging atherectomy catheters also have difficulty imaging through the area of the cutting window during catheter delivery. The sharp edges of the cutter on known atherectomy catheters are typically exposed during imaging and thus prevent simultaneous delivery and imaging by the device, since those exposed edges may accidentally catch and tear into the body lumen. For example, in U.S. Pat. No. 5,634,464, an imaging transducer is mounted on a rotatable cutter. Imaging can be performed either while the cutter is rotated or while it is merely axially translated (without rotation). In either case, the cutting blade is exposed during imaging.

For these reasons, it is desired to provide intravascular catheters which have imaging capability that enables a physician to differentiate between desirable tissue structure and undesirable fatty deposits to be removed from a body lumen. It is desirable that the imaging and cutting of material can occur without having to reposition the catheter between such procedures. It would also be desirable if the atherectomy catheter could interrogate and view the vessel while the cutter is delivered through the body lumen or vasculature. It would still further be desirable to provide atherectomy catheters having imaging capabilities which can be utilized while the blade of the atherectomy device is unexposed to the blood vessel. At least some of these objectives will be met by the catheter and method of the present invention described hereinafter and in the claims.

SUMMARY OF THE INVENTION

The present invention provides catheters, kits, and methods for removing material from a body lumen. More particularly, the present invention provides an atherectomy catheter, such as catheters having axially translatable, non-rotating cutting blades, with an imaging capability so that areas of the body lumen can be imaged and evaluated before the cutting procedure.

In a first aspect, the present invention provides a catheter for use in excising material from a body lumen. The catheter comprises a catheter body, a cutting blade, and an imaging device. The cutting blade is mounted on the catheter body and configured to move between a material capture (open) position and a closed position. When the cutting blade is in the closed position, the blade substantially closes an aperture or "cutting window" on the catheter body. The imaging device which is usually mounted on or coupled to the cutting blade is configured to be in an imaging position when the cutting blade substantially closes the aperture or cutter window. This allows the imaging device to survey material within a "cutting zone" of the atherectomy catheter, preferably precisely at the location where severing of the material will occur, most preferably being aligned with the location of a cutting edge on the cutting blade when the blade is in the capture configuration. By allowing the imaging device to view materials within this cutting zone, preferably precisely at the spot where severing of the material will occur or be initiated, the material may be imaged and then removed from the body lumen without having to reposition the catheter between each step. Furthermore, by having the cutter blade in a substantially closed position, the sharpened edges of the blade are not exposed to the tissue of the body lumen. This advantageously allows the catheter to image tissue while the catheter is delivered through tortuous vasculature without risk that the sharpened edge of the cutting blade will accidentally penetrate tissue during the delivery process.

In one embodiment, the present invention provides a catheter having a telescoping cutting blade that extends outwardly from an aperture on the catheter body. The cutting blade has a first open position leaving a gap between the blade and the catheter body to define a cutting window. Material targeted for removal will intrude into the cutter window and be sheared off when the telescoping cutting blade is retracted into a second closed position. The cutting window defined by the gap is typically a directional, side-opening cutting window. The material imaging device is typically located at a distal end of the telescoping cutting blade. In this embodiment, the material imaging device can provide information regarding the body lumen when the cutting blade is an open or a closed position.

In another embodiment, a catheter of the present invention comprises a catheter body having a side-opening aperture having a cutting blade for shearing off material that intrudes into the aperture or cutting window. A material imaging device is coupled to the cutting blade so that the imaging device will be in an imaging position when the blade substantially closes the cutting window. The imaging device in this embodiment is located behind the cutting edge of the cutting blade.

In another aspect, the present invention provides a method for removing material from a body lumen. The method comprises positioning a catheter body having a cutting blade adjacent to a target material in the body lumen. The cutting blade has a material imaging device and the blade is mounted on the catheter body to excise material which enters a cutting window defined at least in part by the catheter body. The material is imaged when the cutting blade substantially closes the cutting window. It should be understood of course that the material imaging device could be a variety of sensors such as an ultrasound transducer array or optical fibers for optical coherence tomography. The imaging typically occurs prior to cutting. The cutting blade is then withdrawn to allow material to intrude into the cutting window for cutting and removal.

In a still further aspect, kits according to the present invention will comprise a catheter having a material imaging device. The kits will further include instructions for use setting forth a method as described above. Optionally, the kits will further include packaging suitable for containing the catheter and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the catheter will be provided in a sterilized condition. Other kit components, such as a guidewire or material imaging accessories, may also be included.

A further understanding of the nature and advantages of the invention will become apparent by reference to the remaining portions of the specification and drawings.

BRIEF DESCRIPTION OF THE DRAWINGS

FIGS. 6A–6B are cross-sectional views of a material cutting device having a material imaging device designed for use with a side-opening cutter window.

FIGS. 11A–12B show embodiments of the catheter having a material capture device and a material imaging device.

DESCRIPTION OF THE SPECIFIC EMBODIMENTS

Figure 1:
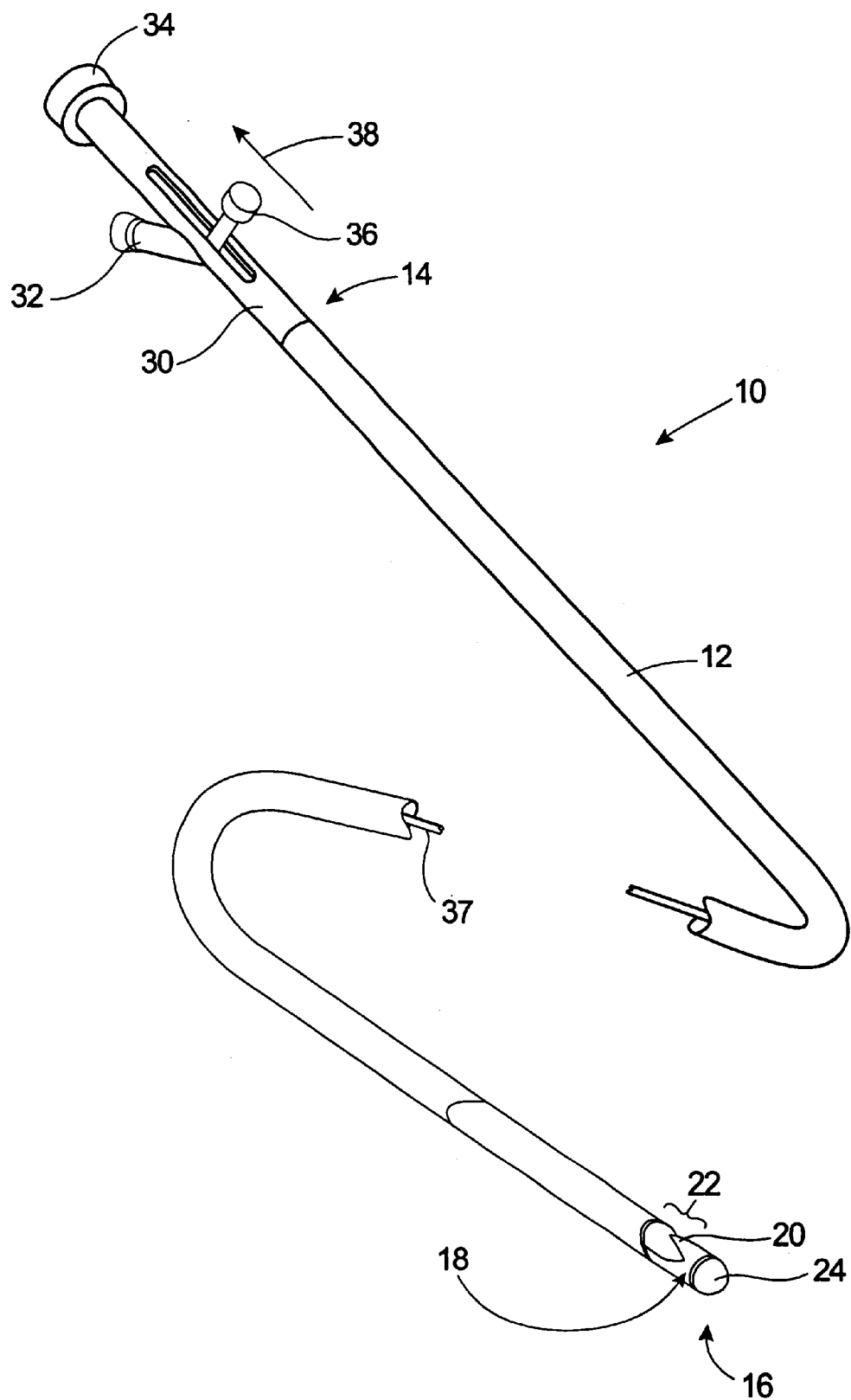
FIG. 1 is a perspective view of an atherectomy catheter constructed in accordance with the principles of the present invention.

The present invention is generally directed to excising material from a body lumen. More particularly, the present invention provides catheters, methods, and kits for imaging material to be removed from a body lumen prior to performing the removal or cutting procedure. The present invention advantageously allows for the imaging of material to be cut prior to the cutting or removal procedure. Furthermore, the material may be imaged and then cut without requiring the repositioning of the catheter body as commonly required in conventional intravascular catheters.

Apparatus according to the present invention will comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the catheter bodies will typically be very flexible and suitable for introduction over a guidewire to a target site within the vasculature. In particular, catheters can be intended for "over-the-wire" introduction when a guidewire lumen extends fully through the catheter body or for "rapid exchange" introduction where the guidewire lumen extends only through a distal portion of the catheter body.

Catheter bodies intended for intravascular introduction will typically have a length in the range from 50 cm to 200 cm and an outer diameter in the range from 1 French (0.33 mm; Fr.) to 12 Fr., usually from 3 Fr. to 9 Fr. In the case of coronary catheters, the length is typically in the range from 125 to 200 cm, the diameter is preferably below 8 Fr., more preferably below 7 Fr., and most preferably in the range from 2 Fr. to 7 Fr. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, axial filaments, or the like, in order to increase rotational strength, column strength, toughness, pushability, and the like. Suitable catheter bodies may be formed by extrusion, with one or more lumens being provided when desired. The catheter diameter can be modified by heat expansion and shrinkage using conventional techniques. The resulting catheters will thus be suitable for introduction to the vascular system, often the coronary arteries, by conventional techniques.

The cutting blades used in the present invention will usually be formed from a metal, but could also be formed from hard plastics, ceramics, or composites of two or more materials, which can be honed or otherwise formed into the desired cutting edge. In the exemplary embodiments, the cutting blades are formed as coaxial tubular blades with the cutting edges defined in aligned apertures therein. It will be appreciated that the present invention is not limited to such preferred cutting blade assemblies, in a variety of other designs, such as the use of wiper blades, scissor blades or the like. Optionally, the cutting edge of either or both the blades may be hardened, e.g., by application of a coating. A preferred coating material is titanium nitride, available from Brycoat, Inc., which may be applied according to manufacturer's instructions.

The present invention may employ any of a wide variety of conventional imaging devices and transducers. It will be particularly useful with phased array transducers of a type which may be deployed linearly or circumferentially on the cutting blade. Linear deployment will allow viewing along a discrete length of the catheter axis, preferably adjacent to the cutting point, usually over a length in the range from 1 mm to 30 mm, preferably 2 mm to 10 mm. Circumferentially deployed phased arrays may subtend a viewing arc in the range from 5° to 360°, usually from 180° to 360° in the case of telescoping cutters (e.g., FIGS. 1–5) or 90° to 180° in the case of window cutters (FIGS. 6A, 6B, 9A, 9B, 10A, 10B, 11A, 11B, and 12A, 12B. The ability to image over a full 360° can be achieved with the catheters having cutting blades which extend fully from a fixed portion of the cutter assembly, such as those illustrated in FIGS. 2–4. For imaging transducers located on cutting blades within a housing or second cutting element, the field of imaging will generally be limited by the dimensions of the aperture. In some cases, however, it might be possible to fabricate all or a portion of the cutter blade/housing out of an ultrasonically translucent material. In addition to ultrasonic array transducers, the imaging devices of the present invention may comprise optical coherence tomography devices, such as described in U.S. Pat. No. 5,491,524, the full disclosure of which is incorporated herein by reference, as well as Huang et al. (1991) Science 254:1178–1181; Brezinski et al. (1997) Heart 77:397–403; and Brezinski et al (1996) Circulation 93:1206–1213. In some instances, the present invention may also provide optical imaging using optical wave guides and the like.

Referring now to FIG. 1, a catheter 10 constructed in accordance with principles of the present invention, comprises a catheter body 12 having a proximal end and a distal end 16. In the embodiment shown in FIG. 1, a telescoping cutting mechanism 18 is mounted on the distal end of the catheter body. The cutting mechanism or cutting blade 18 has a proximal pointing cutting edge 20 which may be spaced apart from the catheter body to define a cutting window 22. Preferably, the cutting mechanism 18 has an atraumatic distal tip 24 to facilitate the introduction of the catheter through a patient's vasculature. A proximal hub 30 is attached to the proximal end of the catheter body and comprises a perfusion/aspiration connector 32, a guidewire connector 34, and a slider 36. The slider 36 is attached to the proximal end of an actuator rod 37 which extends from the hub 30 through the lumen of catheter body 12 into the cutting mechanism 18 where it is attached at a proximal end of the inner cutter 22. In this way, manual actuation of slider 36 in the direction of arrow 38 moves inner cutter 22 in the direction of arrow 40.

Figure 2:
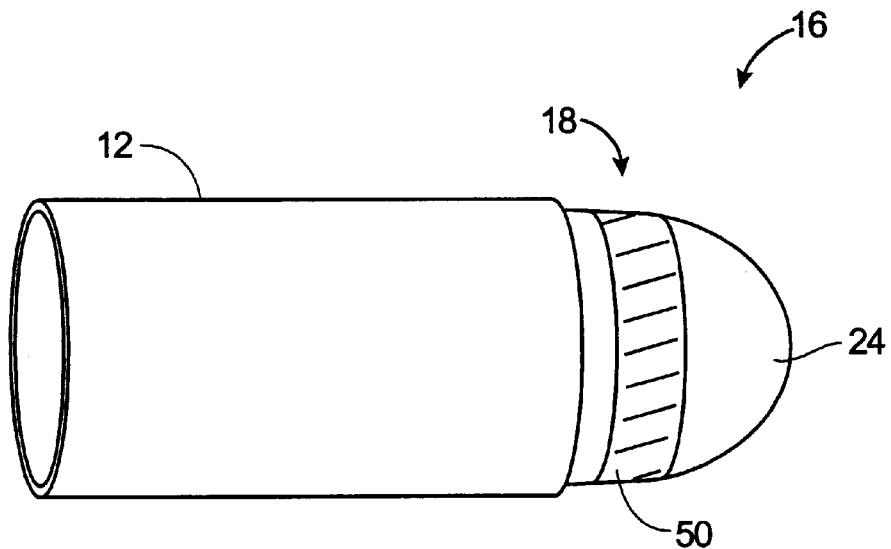
FIGS. 2–5 show various embodiments of a catheter having a telescoping, material cutting element having a material imaging device according to the present invention.
Figure 3:
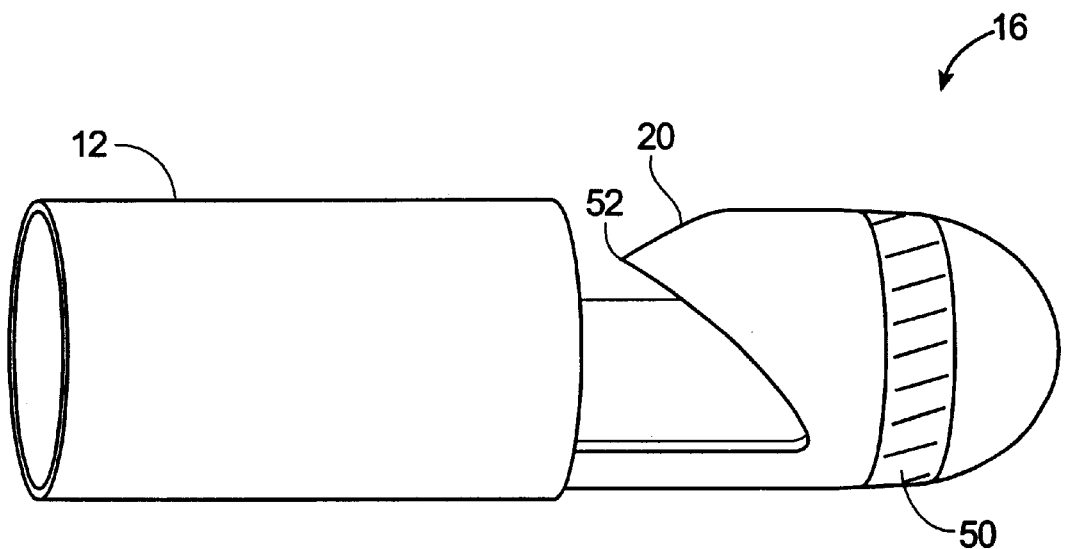

Referring now to FIGS. 2 and 3, the distal end 16 of the catheter shown in FIG. 1 will be described in further detail. FIG. 2 shows the cutter mechanism 18 in a first closed position relative to the catheter body 12. In this position, the sharpened edges of the cutting mechanism 18 is contained within the catheter body 12. The atraumatic distal tip 24 may be equipped with a material imaging device such as an ultrasound transducer array or an optical coherence tomography device. In other embodiments, a multiple, phased ultrasound array may be used to provide imaging. As can be seen in FIGS. 2 and 3, the material imaging device 50 can provide images when the cutting blade or cutting mechanism 18 is in a first closed position as shown in FIG. 2 or in an open, material-engaging position as shown in FIG. 3. As best seen in FIG. 2, when the cutter mechanism 18 is closed, the imaging device 50 will lie adjacent to the leading edge of the catheter body 12, where the catheter body acts as the second blade to effect severing of the material. Thus, the material imaging device 50 will be positioned right at the point where material will be severed. The cutting edge 20 as shown in FIG. 3, typically includes a penetrating point 52 to facilitate material capture. By locating the material imaging device 50 on the cutting blade 18, the present invention can move the imaging device through the various paths or cutting zones if the cutting blade were actuated. This ability to move the imaging device 50 allows for imaging and cutting of the targeted material without having to reposition the catheter body 12 which may cause misalignment of those materials imaged before cutting and the actual location of the cutting zone. Of course, the material imaging device 50 can be used at any point during the procedure, either before or after severing of the target material and an image could be produced even while the cutting blade is being moved between the open and closed positions of the cutting mechanism 18.

Figure 4:
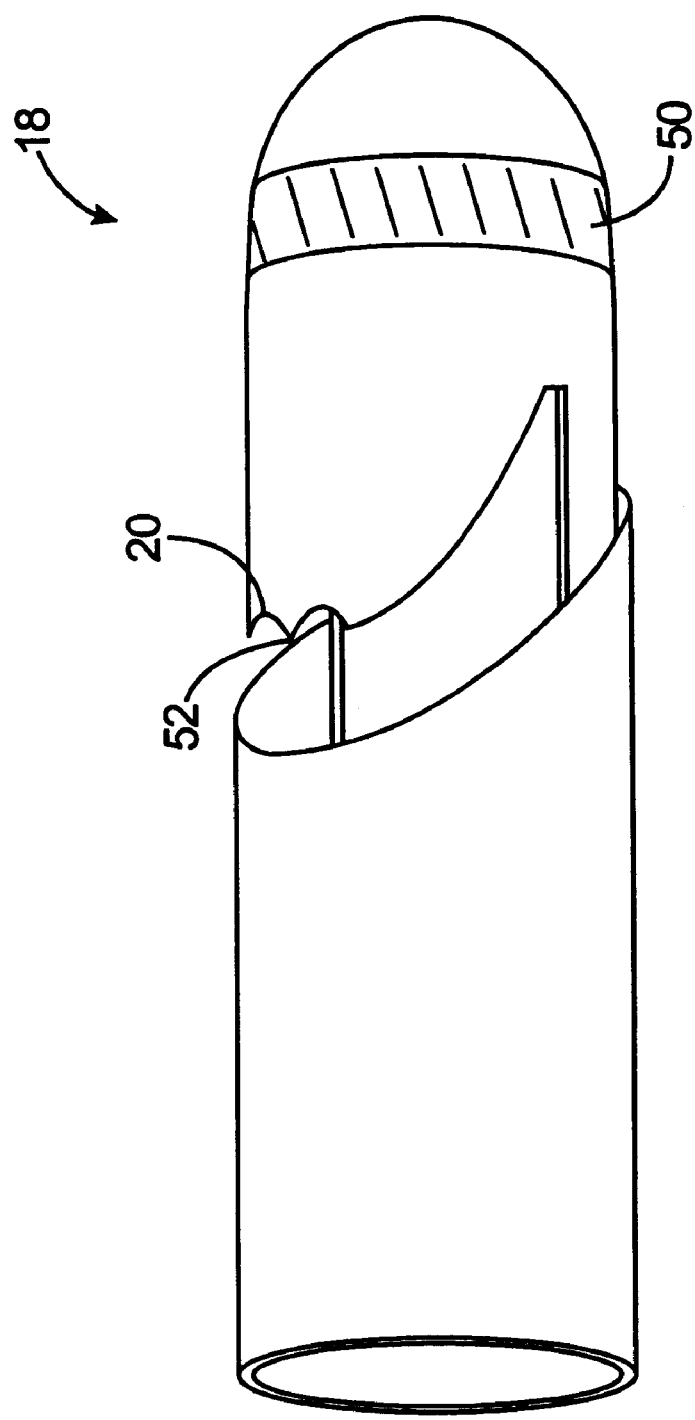

The cutting edge 20 on the cutting blade 18 may be designed to have a plurality of penetrating points 52 as shown in FIG. 4 or may be otherwise configured to maximize material capture. Suitable cutting blade and cutting edge designs can be found in commonly assigned copending U.S. patent application Ser. No. 08/982,231 (Attorney Docket No. 18489-200US) filed on Dec. 17, 1997, which is incorporated herein by reference.

Figure 5:
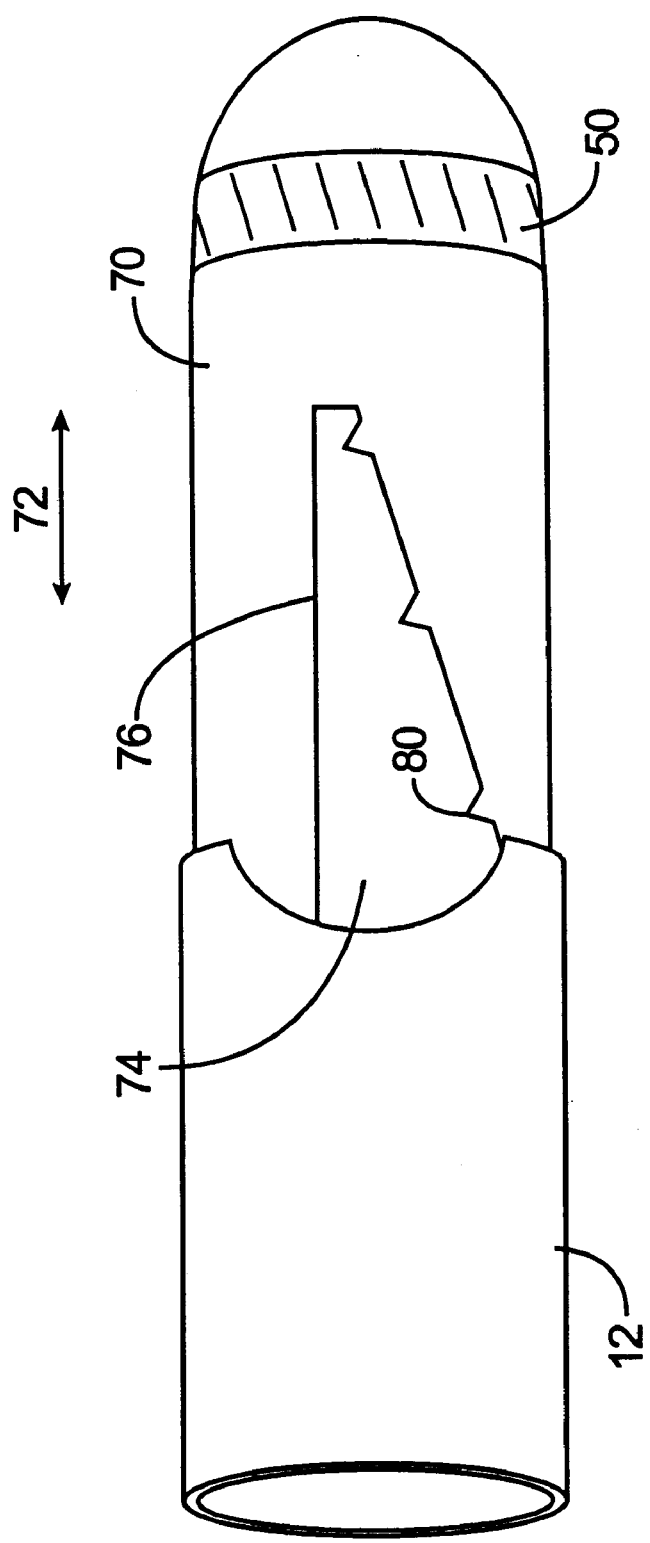

Referring now to FIG. 5, another embodiment of the cutting mechanism or cutting blade according to the present invention will now be described. As seen in FIG. 5, the cutting mechanism 70 may reciprocate as indicated by arrows 72. This telescoping cutter mechanism 70 moves in a linear fashion to shear those materials which may enter the cutting window 74 defined by the cutting edge 76 and the catheter body 12. A material imaging device 50 is located in the tip of the cutting mechanism 70. By linearly reciprocating the cutting mechanism 70, a physician or operator could view the cut area pre-removal and post-removal without moving the entire catheter body. The cutting edge 76 of the present invention includes a plurality of penetrating points 80 which may angled or bent to pierce material in an effort to move the material in a certain direction, such as toward the capture area as well as initiate the cutting of the material.

Although the embodiments described thus far show a telescope cutting blade extending outwardly from a forward-facing aperture of a catheter body, it should be understood that a variety of other configurations may also be adapted for use with a material imaging device. Referring now to FIGS. 6A and 6B, an atherectomy catheter 100 has an inner cutter 102 mounted coaxially within an outer cutter 104 on the catheter body. The catheter 100 includes an atraumatic distal tip 106 to facilitate introduction of the catheter through a patient's vasculature. As seen if FIG. 6A, a material imaging device 110 is located on the inner cutter 102. When the inner cutter or cutter blade is positioned to close the cutter window or aperture 112 (FIG. 6B) the imaging device 110 is in position to survey materials in the cutting zone of the catheter 100. In this position, the physician can inspect the material to be removed and verify or fine tune the positioning of the catheter 100 to accurately target material for removal. When it is verified that the catheter 100 is in the proper position, the inner cutter 102 is moved to an open position where a material may intrude into the cutting window or aperture 112 which will then be sheared off when the inner cutter is reciprocated to move into a closed position. A flex wire or flex circuit 120 is connected to the material imaging device 110.

Figure 7A:
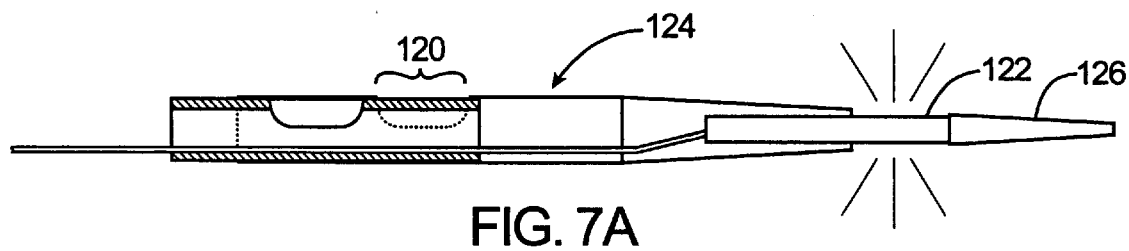
FIGS. 7A–8B depict embodiments of a material cutting device where the material imaging device extends outwardly from a forward-facing, distal opening on the catheter body.
Figure 7B:
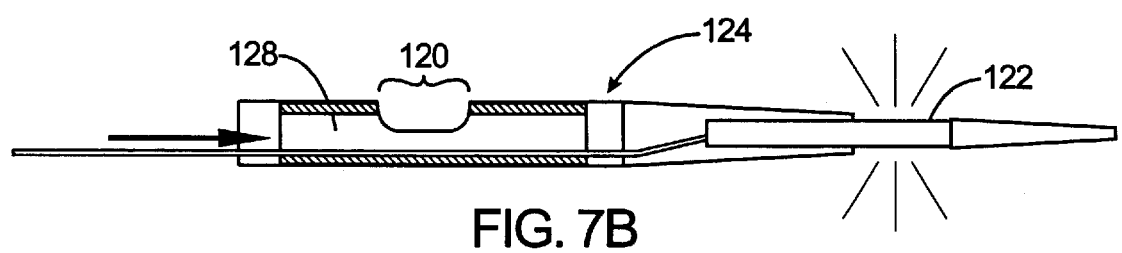

Referring now to FIGS. 7A and 7B, a material excising catheter having a side-opening cutting window 120 is equipped with a material imaging device 122 that extends outward from a forward-facing, distal aperture of a catheter body 124. The material imaging device 122 has a soft, atraumatic distal tip 126 to facilitate introduction through the patient's vasculature. Positioning the imaging device 122 in the manner shown in FIG. 7A allows for full time 360° imaging for diagnostic purposes. (Such a design allows for incorporation of an imaging device without having to change the structure of the inner cutter 128 and most of the catheter body 124.)

Figure 8A:
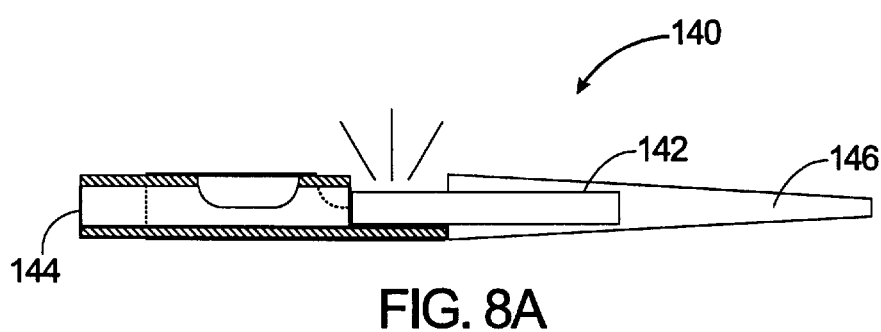
Figure 8B:
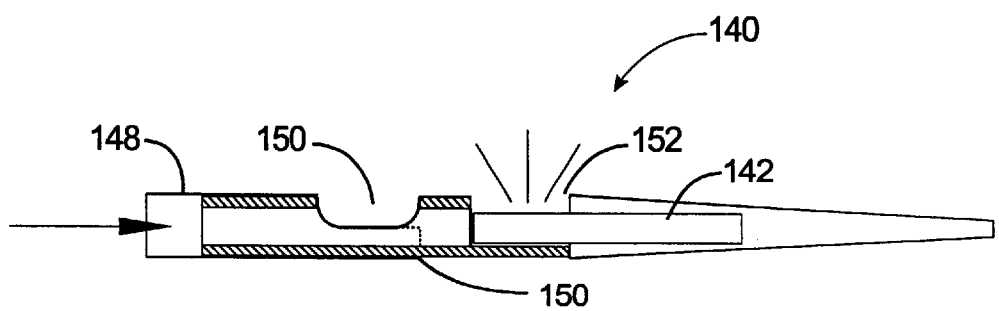

Referring now to FIGS. 8A and 8B, a still further embodiment of a material excising catheter will be described. As shown in FIG. 8A, the catheter 140 has a material imaging device 142 mounted on the inner cutter 144 and coupled to the atraumatic distal tip 146. The imaging device 142 is spaced apart from the distal tip, and thus differs from the embodiment shown in FIG. 1 through FIG. 3. The catheter configuration shown in FIGS. 8A and 8B, the imaging device is mounted to the soft tip 146 and inner cutter 144 such that the target material or atheroma is viewed when the cutter is retracted (FIG. 8A). This allows the physician to view material through the cutter window prior to and after the cutting procedure. Additionally, because the outer cutter 148 has an open distal end 150 the material imaging device 142 can provide full time material imaging, whether the inner cutter is in a closed or an open position. The inner cutter 144, as shown in FIG. 8B, has a first and second aperture 150 and 152. The side-opening aperture 150 is provided for material removal while aperture 152 is provided for the material imaging device 142. In FIG. 8B, the material imaging device 142 is fully extended outside the catheter body or outer cutter 148. In this position, the material imaging device 142 can be configured for partial or 360° material imaging.

Figure 9A:
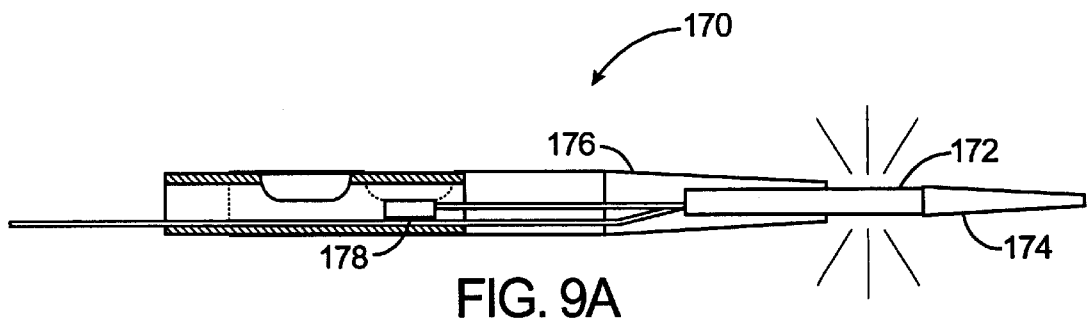
FIGS. 9A–10B show embodiments of the catheter using a plurality of imaging devices.
Figure 9B:
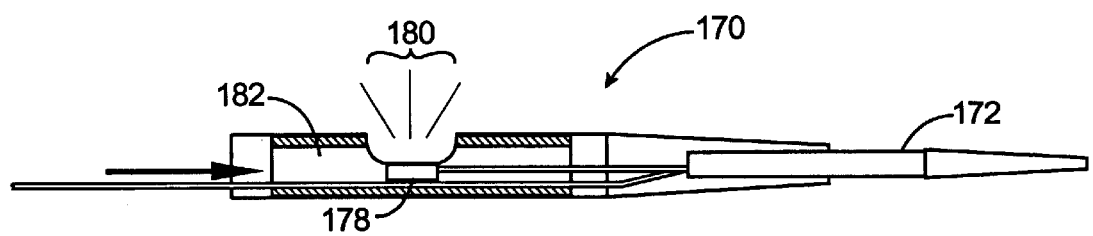

Referring now to FIGS. 9A through 10B, still further embodiments of a material excising catheter according to the present invention will be described. FIGS. 9A and 9B show a catheter 170 having a first material imaging device 172 coupled to the soft, atraumatic distal end 174. A second material imaging device 178 is positioned opposite a side-opening cutter window 180 on the catheter body 176. The distal-most imaging device 172 can be used to image the vessel and make an initial determination of where to cut material from the vessel wall. After making the initial determination, the inner cutter 182 is moved to an opened position (FIG. 9B) the cutter window 180 will be opened and the imaging device 178 exposed so that it may be used for imaging. The catheter will usually be repositioned so that the imaging device 178, which is located at the cutting position, is aligned with the material originally located with the distal-most imaging device 172. Once it is verified that the target material to be removed is positioned within the cutting aperture, the inner cutter 182 may be translated to sever the material.

Figure 10A:
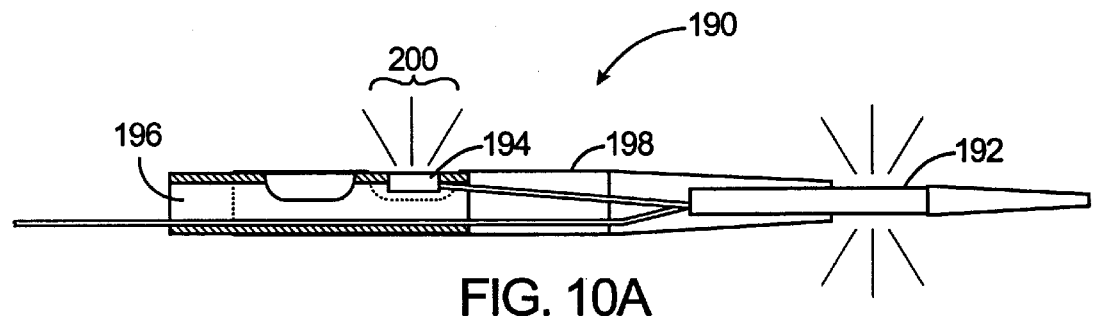
Figure 10B:
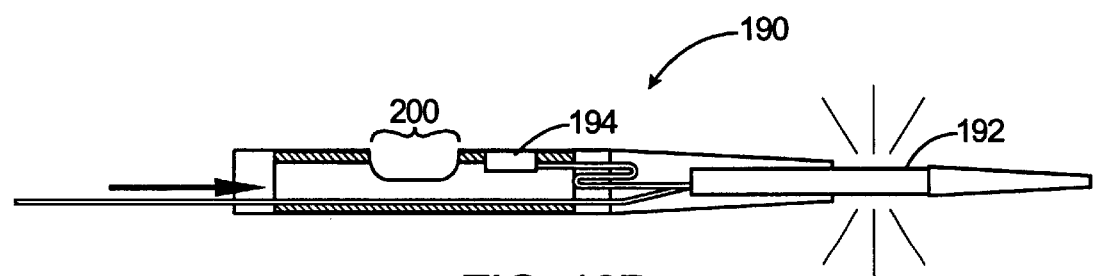

FIGS. 10A and 10B show a catheter 190 having a plurality of imaging devices 192 and 194. Locations of these imaging devices are similar to those described above for catheter 170 in FIGS. 9A and 9B, except that the second imaging device 194 is mounted on the inner cutter 196 instead of on the catheter body 198. As seen in FIG. 10A, the second material imaging device 194 is in an imaging position when the inner cutter 196 has closed the side-opening cutter window 200 (FIG. 10A). Advantageously, by enclosing the cutting window 200 and drawing the sharpened edges of the cutter into the catheter body, the catheter 190 may be delivered more smoothly through the vasculature with reduced risk that one of those cutter edges will catch a body tissue, while the catheter 190 can continue to image the vasculature during delivery.

FIGS. 11A through 12B show a preferred embodiment of the present invention having an imaging device 220 mounted on the inner cutter 222 (FIG. 11B) for imaging material when the cutter window 224 is closed by the inner cutter (FIG. 12B). As seen in FIGS. 11B and 12B, this embodiment of the catheter includes a material capture device 226 and a cam follower 228. A suitable material capture device for use with the present invention can be found in commonly assigned, copending U.S. patent application Ser. No. 09/377884 (Attorney Docket No. 18489-001600) filed on the same day as the present application, the full disclosure of which is incorporated herein by reference. A flex wire 230 couples the material imaging device 220 to monitoring devices located outside of the catheter. Imaging device 220 may be an array of piezoelectric ultrasonic transducer elements operating in a frequency range between 20 MHz to 50 MHz. An exemplary ultrasonic transducer array is described in U.S. Pat. No. 4,917,097 to Proudian et al., the full disclosure of which is incorporated herein by reference. The signals produced by the multiple elements may be processed in a conventional manner such as using a synthetic aperture to produce an image of a sector of the vessel being treated. Usually, the sector will be about 90°, and the device can be rotated to provide a larger view (up to 360°) if desired.

It would also be possible to use rotating ultrasonic transducers, as described in U.S. Pat. No. 5,902,245, the full disclosure of which is incorporated herein by reference, or a single element ultrasonic transducer, optionally to provide a moving B mode where the imaging point is moved over time. Moving B mode imaging may be particularly useful in treating in-stent restenosis where the struts or other elements of the stent are readily apparent, even with such a simple imaging approach. Other imaging approaches include angioscopy, e.g., as described in U.S. Pat. No. 5,263,928, the full disclosure of which is incorporated herein by reference.

Figure 13:
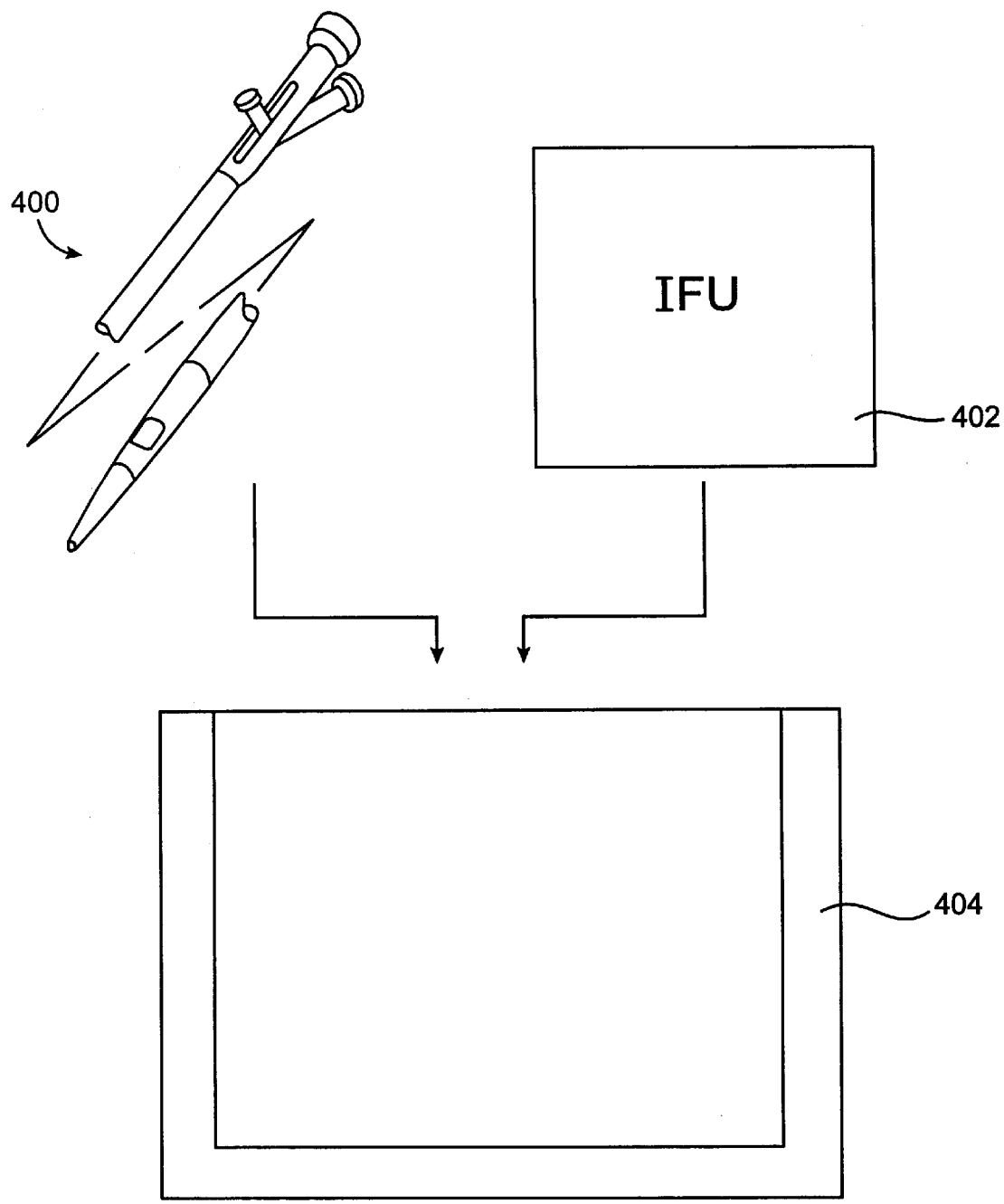
FIG. 13 shows a kit according to the present invention.

Referring now to FIG. 13, the present invention will further comprise kits including catheters 400, instructions for use 402, and packages 404. Catheters 400 will generally be described above, and the instruction for use (IFU) 402 will set forth any of the methods described above. Package 404 may be any conventional medical device packaging, including pouches, trays, boxes, tubes, or the like. The instructions for use 402 will usually be printed on a separate piece of paper, but may also be printed in whole or in part on a portion of the packaging 404.

While all the above is a complete description of the preferred embodiments of the inventions, various alternatives, modifications, and equivalents may be used. Although the foregoing invention has been described in detail for purposes of clarity of understanding, it will be obvious that certain modifications may be practiced within the scope of the appended claims.

What is claimed is:

1. A method of removing material from a body lumen, the method comprising:

positioning a catheter comprising a tissue removal assembly in a body lumen;

rotating the tissue removal assembly;

axially moving the tissue removal assembly in the catheter; and directing the tissue removal assembly radially out of a side-opening cutting window in the catheter.

2. The method of claim 1 wherein the catheter defines an outer diameter, wherein directing comprises moving the tissue removal assembly radially out of the side-opening cutting window beyond an outer diameter of the catheter.

3. The method of claim 1 wherein directing comprises moving at least part of the tissue removal assembly over a ramp disposed within the catheter.

4. The method of claim 1 further comprising imaging the body lumen with an imaging device disposed on at least one of the catheter and tissue removal assembly.

5. The method of claim 1 further comprising removing material from the body lumen with the rotating tissue removal assembly directed out of the cutting window.

6. The method of claim 5 wherein cutting comprises using a non-serrated cutting edge.

7. A medical kit comprising:

a catheter having a catheter body that comprises a side-opening cutting window, an outer diameter, and a movable tissue removal assembly that can extend beyond the outer diameter of the catheter body;

instructions for use in removing material from a body lumen comprising moving the tissue removal assembly between a first position in which the tissue removal assembly is disposed within the catheter body and a second position in which at least a portion of the tissue removal assembly is positioned beyond the outer diameter of the catheter body; and a package adapted to contain the catheter and istructions for use.

8. The kit of claim 7 wherein the tissue removal assembly comprises a cutting blade comprising a non-serrated cutting edge.

9. The kit of claim 7 wherein the catheter further comprises an imaging device disposed on at least one of the catheter body and tissue removal assembly.

10. The kit of claim 7 wherein the instructions further comprise rotating the tissue removal assembly.

11. The kit of claim 7 wherein the catheter further comprises a cam disposed in the catheter body that directs the tissue removal assembly from the first position to the second position.

12. A method of removing tissue from a body lumen, the method comprising:

positioning a catheter in the body lumen;

placing a tissue removal assembly in a first position in which the tissue removal assembly is disposed within the catheter; and moving at least a portion of the tissue removal assembly over a cam in the catheter so as to move the tissue removal assembly to a second position in which the tissue removal assembly extends through a side-opening cutting window in the catheter and beyond an outer diameter of the catheter.

13. The method of claim 12 further comprising imaging the body lumen when the tissue removal assembly is in the first position.

14. The method of claim 12 further comprising rotating the tissue removal assembly during moving.

15. A method of removing material from a body lumen, the method comprising:

positioning a catheter comprising a tissue removal assembly in a body lumen;

rotating the tissue removal assembly;

axially moving the tissue removal assembly in the catheter; and directing the tissue removal assembly radially out of a side-opening cutting window in the catheter, beyond an outer surface of the catheter.

16. The method of claim 15 wherein directing the tissue removal assembly comprises moving at least part of the tissue removal assembly over a ramp disposed within the catheter.

17. The method of claim 15 comprising imaging the body lumen with an imaging device disposed on at least one of the catheter and tissue removal assembly.

18. The method of claim 15 further comprising removing material from the body lumen with the rotating tissue removal assembly directed out of the cutting window.

* * * * *